United States Patent
Aravalli (10) Patent No.: US 11,160,682 B2
(45) Date of Patent: Nov. 2, 2021

(54) METHOD AND APPARATUS FOR ACCESSING MATTER DISPOSED WITHIN AN INTERNAL BODY VESSEL

(71) Applicant: Covidien LP, Mansfield, MA (US)

(72) Inventor: AVVLN Srinivasa Murthy Aravalli, Tanuku (IN)

(73) Assignee: Covidien LP, Mansfield, MA (US)

(*) Notice: Subject to any disclaimer, the term of this patent is extended or adjusted under 35 U.S.C. 154(b) by 578 days.

(21) Appl. No.: 16/000,376

(22) Filed: Jun. 5, 2018

(65) Prior Publication Data
US 2018/0360643 A1 Dec. 20, 2018

Related U.S. Application Data

(60) Provisional application No. 62/521,755, filed on Jun. 19, 2017.

(51) Int. Cl.
*A61F 5/445* (2006.01)
*A61B 17/04* (2006.01)
(Continued)

(52) U.S. Cl.
CPC .......... *A61F 5/445* (2013.01); *A61B 17/0469* (2013.01); *A61B 17/1155* (2013.01);
(Continued)

(58) Field of Classification Search
CPC .......... A61F 5/445; A61F 5/448; A61F 5/449; A61B 17/0469; A61B 17/1155; A61B 17/3415
(Continued)

(56) References Cited

U.S. PATENT DOCUMENTS

| 3,402,710 A | 9/1968 | Paleschuck |
| 3,495,586 A | 2/1970 | Regenbogen |

(Continued)

FOREIGN PATENT DOCUMENTS

| CA | 2702419 A1 | 11/2010 |
| EP | 0226026 A2 | 6/1987 |

(Continued)

OTHER PUBLICATIONS

Extended European Search Report issued in European Application No. 18178344.0 dated Nov. 29, 2018.

*Primary Examiner* — Andrew J Mensh
(74) *Attorney, Agent, or Firm* — Carter, DeLuca & Farrell LLP (57) ABSTRACT

A method for accessing matter within an intestine, includes creating an opening extending through an abdominal wall of an abdominal cavity, accessing an intestinal end segment of an intestine within the abdominal cavity, positioning the intestinal end segment of the intestine in registration with the opening extending through the abdominal wall, attaching the intestinal end segment to cutaneous tissue surrounding the opening to establish fluid communication between a lumen of the intestine and the opening through the abdominal wall, securing an access device adjacent the opening through the abdominal wall and connecting a receptacle to the access device configured to be in fluid communication with the lumen of the intestine to collect matter within the intestine.

15 Claims, 9 Drawing Sheets

(51) Int. Cl.
  *A61B 17/34* (2006.01)
  *A61B 17/115* (2006.01)
  *A61F 5/449* (2006.01)
  *A61F 5/448* (2006.01)
  *A61F 2/00* (2006.01)
  *A61B 17/11* (2006.01)
  *A61B 17/068* (2006.01)

(52) U.S. Cl.
  CPC .......... *A61B 17/3415* (2013.01); *A61F 5/448* (2013.01); *A61F 5/449* (2013.01); *A61B 17/0487* (2013.01); *A61B 17/068* (2013.01); *A61B 17/1114* (2013.01); *A61F 2/0063* (2013.01); *A61F 2005/4455* (2013.01)

(58) Field of Classification Search
  USPC .......................................................... 604/332
  See application file for complete search history.

(56) References Cited

U.S. PATENT DOCUMENTS

| | | |
|---|---|---|
| 4,016,884 A | 4/1977 | Kwan-Gett |
| 4,112,932 A | 9/1978 | Chiulli |
| 4,183,357 A * | 1/1980 | Bentley .................. A61F 5/445 604/175 |
| 4,209,010 A * | 6/1980 | Ward .................. A61F 2/0013 128/DIG. 25 |
| 4,217,664 A * | 8/1980 | Faso .................. A61F 2/0063 600/32 |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |

(56) References Cited

U.S. PATENT DOCUMENTS

| | | |
|---|---|---|
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |

(56) References Cited

U.S. PATENT DOCUMENTS

| | | | |
|---|---|---|---|
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0220621 A1* | 11/2003 | Arkinstall .......... A61F 5/445 604/335 |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0225277 A1* | 11/2004 | Jacob .......... A61B 17/3421 604/506 |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0275795 A1* | 11/2009 | Martino .......... A61F 5/445 600/32 |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0306823 A1* | 12/2011 | Gobel .......... A61F 5/445 600/32 |
| 2011/0313250 A1 | 12/2011 | Kleyman |

(56) References Cited

U.S. PATENT DOCUMENTS

| | | | |
|---|---|---|---|
| 2012/0059640 A1 | 3/2012 | Roy et al. | |
| 2012/0130177 A1 | 5/2012 | Davis | |
| 2012/0130181 A1 | 5/2012 | Davis | |
| 2012/0130182 A1 | 5/2012 | Rodrigues, Jr. et al. | |
| 2012/0130183 A1 | 5/2012 | Barnes | |
| 2012/0130184 A1 | 5/2012 | Richard | |
| 2012/0130185 A1 | 5/2012 | Pribanic | |
| 2012/0130186 A1 | 5/2012 | Stopek et al. | |
| 2012/0130187 A1 | 5/2012 | Okoniewski | |
| 2012/0130188 A1 | 5/2012 | Okoniewski | |
| 2012/0130190 A1 | 5/2012 | Kasvikis | |
| 2012/0130191 A1 | 5/2012 | Pribanic | |
| 2012/0136324 A1* | 5/2012 | Hanuka | A61F 5/441 604/318 |
| 2012/0149987 A1 | 6/2012 | Richard et al. | |
| 2012/0157777 A1 | 6/2012 | Okoniewski | |
| 2012/0157779 A1 | 6/2012 | Fischvogt | |
| 2012/0157780 A1 | 6/2012 | Okoniewski et al. | |
| 2012/0157781 A1 | 6/2012 | Kleyman | |
| 2012/0157782 A1 | 6/2012 | Alfieri | |
| 2012/0157783 A1 | 6/2012 | Okoniewski et al. | |
| 2012/0157784 A1 | 6/2012 | Kleyman et al. | |
| 2012/0157785 A1 | 6/2012 | Kleyman | |
| 2012/0157786 A1 | 6/2012 | Pribanic | |
| 2012/0190931 A1 | 7/2012 | Stopek | |
| 2012/0190932 A1 | 7/2012 | Okoniewski | |
| 2012/0190933 A1 | 7/2012 | Kleyman | |
| 2012/0209077 A1 | 8/2012 | Racenet | |
| 2012/0209078 A1 | 8/2012 | Pribanic et al. | |
| 2012/0245427 A1 | 9/2012 | Kleyman | |
| 2012/0245429 A1 | 9/2012 | Smith | |
| 2012/0245430 A1 | 9/2012 | Kleyman et al. | |
| 2012/0283520 A1 | 11/2012 | Kleyman | |
| 2013/0060212 A1 | 3/2013 | Hanuka et al. | |
| 2013/0197458 A1* | 8/2013 | Salama | A61F 5/4405 604/335 |
| 2013/0225930 A1 | 8/2013 | Smith | |
| 2013/0225931 A1 | 8/2013 | Cruz et al. | |
| 2013/0245373 A1 | 9/2013 | Okoniewski | |
| 2013/0274559 A1 | 10/2013 | Fowler et al. | |
| 2013/0310651 A1 | 11/2013 | Alfieri | |
| 2014/0018632 A1 | 1/2014 | Kleyman | |
| 2015/0053747 A1* | 2/2015 | Prior | A61B 17/3431 227/179.1 |

FOREIGN PATENT DOCUMENTS

| | | | |
|---|---|---|---|
| EP | 0538060 A1 | 4/1993 | |
| EP | 0577400 A1 | 1/1994 | |
| EP | 0630660 A1 | 12/1994 | |
| EP | 0807416 A2 | 11/1997 | |
| EP | 0950376 A1 | 10/1999 | |
| EP | 1188415 A2 | 3/2002 | |
| EP | 1312318 A1 | 5/2003 | |
| EP | 1774918 A1 | 4/2007 | |
| EP | 1932485 A1 | 6/2008 | |
| EP | 2044889 A1 | 4/2009 | |
| EP | 2044897 A1 | 4/2009 | |
| EP | 2080494 A1 | 7/2009 | |
| EP | 2095781 A2 | 9/2009 | |
| EP | 2098182 A2 | 9/2009 | |
| EP | 2138117 A1 | 12/2009 | |
| EP | 2138118 A2 | 12/2009 | |
| EP | 2181657 A2 | 5/2010 | |
| EP | 2226025 A1 | 9/2010 | |
| EP | 2229900 A1 | 9/2010 | |
| EP | 2238924 A1 | 10/2010 | |
| EP | 2238925 A1 | 10/2010 | |
| EP | 2238926 A2 | 10/2010 | |
| EP | 2238933 A1 | 10/2010 | |
| EP | 2248478 A1 | 11/2010 | |
| EP | 2248482 A1 | 11/2010 | |
| EP | 2253283 A1 | 11/2010 | |
| EP | 2272450 A2 | 1/2011 | |
| EP | 2277464 A1 | 1/2011 | |
| EP | 2289438 A1 | 3/2011 | |
| EP | 2292165 | 3/2011 | |
| EP | 2343019 | 7/2011 | |
| EP | 2856985 A1 | 4/2015 | |
| GB | 2469083 | 4/2009 | |
| WO | 8401512 | 4/1984 | |
| WO | 9314801 | 8/1993 | |
| WO | 9404067 | 3/1994 | |
| WO | 9610963 | 4/1996 | |
| WO | 9636283 | 11/1996 | |
| WO | 9733520 | 9/1997 | |
| WO | 9742889 | 11/1997 | |
| WO | 9916368 | 4/1999 | |
| WO | 9922804 | 5/1999 | |
| WO | 9929250 | 6/1999 | |
| WO | 0032116 | 6/2000 | |
| WO | 0032120 | 6/2000 | |
| WO | 0054675 | 9/2000 | |
| WO | 0108581 | 2/2001 | |
| WO | 0149363 | 7/2001 | |
| WO | 0207611 | 1/2002 | |
| WO | 03034908 A2 | 5/2003 | |
| WO | 03071926 | 9/2003 | |
| WO | 03077726 | 9/2003 | |
| WO | 2004043275 | 5/2004 | |
| WO | 2004054456 | 7/2004 | |
| WO | 2004075741 | 9/2004 | |
| WO | 2004075930 | 9/2004 | |
| WO | 2005058409 | 6/2005 | |
| WO | 2006019723 | 2/2006 | |
| WO | 2006100658 A2 | 9/2006 | |
| WO | 2006110733 | 10/2006 | |
| WO | 2007018458 | 2/2007 | |
| WO | 2007095703 | 8/2007 | |
| WO | 2007143200 | 12/2007 | |
| WO | 2008015566 A2 | 2/2008 | |
| WO | 2008042005 | 4/2008 | |
| WO | 2008077080 | 6/2008 | |
| WO | 2008093313 | 8/2008 | |
| WO | 2008103151 | 8/2008 | |
| WO | 2008121294 A1 | 10/2008 | |
| WO | 2008147644 | 12/2008 | |
| WO | 2009036343 | 3/2009 | |
| WO | 2010000047 | 1/2010 | |
| WO | 2010141409 | 12/2010 | |
| WO | 2010141673 | 12/2010 | |
| WO | 2017079532 A1 | 5/2017 | |

* cited by examiner

METHOD AND APPARATUS FOR ACCESSING MATTER DISPOSED WITHIN AN INTERNAL BODY VESSEL

TECHNICAL FIELD

The present disclosure generally relates to a surgical procedure and associated apparatus for accessing internal body vessels. More specifically, the present disclosure relates to a surgical procedure and an apparatus for performing an ostomy for removal of waste material from an intestine.

BACKGROUND

Exteriorization of an internal body vessel such as the intestine is called a stoma. Stomas may be created in conjunction with an ostomy procedure by inverting and suturing a bisected portion of an intestine to the exterior of the abdominal wall to provide internal access into the intestine for collecting fecal matter. Complications associated with stomas can include leaks, bleeding, necrosis, stenosis, dermal infection, prolapse, etc. Accordingly, a need exists to develop improved methods for reducing risks and complications typically associated with ostomy procedures.

SUMMARY

Accordingly, the present disclosure is directed to a method for accessing matter within an intestine, including creating an opening extending through an abdominal wall of an abdominal cavity, accessing an intestinal end segment of an intestine within the abdominal cavity, positioning the intestinal end segment of the intestine in registration with the opening extending through the abdominal wall, attaching the intestinal end segment to cutaneous tissue surrounding the opening to establish fluid communication between a lumen of the intestine and the opening through the abdominal wall, securing an access device adjacent the opening through the abdominal wall and connecting a receptacle to the access device configured to be in fluid communication with the lumen of the intestine to collect matter within the intestine.

In embodiments, the method includes coupling the intestinal end segment of the intestine to an anvil of a stapling instrument, connecting the anvil to a stapling instrument and firing the stapling instrument to deliver fasteners through the cutaneous tissue surrounding the opening and within the intestinal end segment of the intestine.

In some embodiments, securing the access device includes positioning a connector segment of the access device through the opening and within the lumen of the intestinal end segment of the intestine.

In certain embodiments, the method includes establishing a fluid tight seal about the connector segment of the access device within the lumen of the intestinal end segment of the intestine. In embodiments, establishing the fluid tight seal includes inflating an inflatable bladder disposed about the connector segment of the access device to engage an inner wall of the intestinal end segment. In some embodiments, establishing the fluid tight seal includes suturing the intestinal end segment of the intestine to the connector segment of the access device. In certain embodiments, establishing the fluid tight seal includes adhering the connector segment of the access device within the lumen of the intestinal end segment of the intestine.

In embodiments, coupling the intestinal end segment of the intestine includes arranging the intestinal end segment about an anvil head of the anvil. In some embodiments, firing the stapling instrument includes approximating the anvil head relative to a staple cartridge of the stapling instrument. In certain embodiments, firing the stapling instrument includes delivering an annular array of staples where the staples are at least partially deformed by the anvil head of the anvil. In embodiments, attaching the intestinal end segment of the intestine includes applying a purse string about the intestinal end segment and the anvil head.

In certain embodiments, firing the stapling instrument includes delivering staples through facial tissue underlying the cutaneous tissue.

In some embodiments, positioning the intestinal end segment includes exposing end margins of the intestinal end segment external of the opening, and wherein firing the stapling instrument includes delivering the fasteners through the end margins of the intestinal end segment.

In some embodiments, the method includes attaching a mesh to the intestinal end segment and to muscle tissue beneath the cutaneous tissue.

The method and associated apparatuses for forming an ostomy to collect matter from an intestine according to the present disclosure obviates the need to invert the end margins and create a stoma by directly attaching the intestinal segment to the skin or cutaneous layer about an ostomy extending through the abdominal wall. Thus, complications typically associated with stoma formation including, e.g., leakage of intestinal fluids, infections and other dermal complications, are avoided. The access device utilized in the methodologies supports the intestinal segment during treatment and provides a mechanism to attach to a collection or ostomy bag without producing undue strain on the abdominal wall thereby preserving the integrity of the ostomy.

Other advantages will be appreciated by the following description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Aspects of the present disclosure are described in detail with reference to the drawings, in which like reference numerals designate identical or corresponding elements in each of the several views. As used herein, the term "distal" or "leading" refers to that portion of the device that is farther from the user, while the term "proximal" or "trailing" refers to that portion of the device that is closer to the user. As used herein, the term "clinician" refers to a doctor, nurse, or other care provider and may include support personnel. In the following description, well-known functions or constructions are not described in detail to avoid obscuring the present disclosure in unnecessary detail.

The following discussion will focus on methodologies and associated apparatus(es) in performing an ostomy procedure, particularly, in securing the end margins of an intestine to abdominal tissue in connection with a colostomy or ileostomy procedure. However, the guide apparatus has application in other ostomy procedures including urostomy, gastrostomy and jejunostomy procedures.

Figure 1:
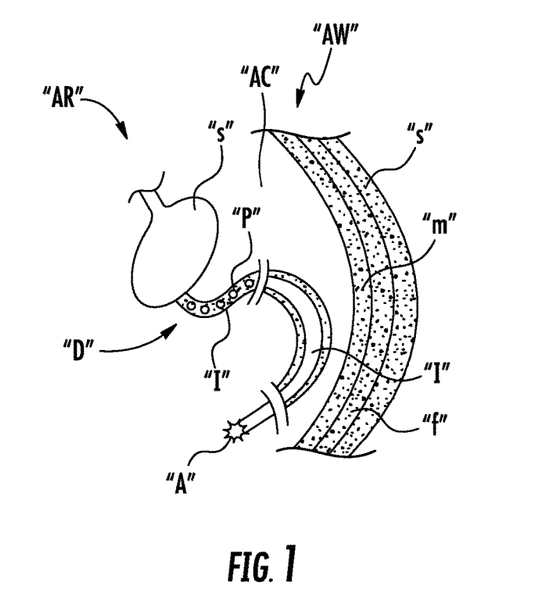
FIG. 1 is a schematic illustration, in partial cross-section, of an abdominal region of a subject.

Referring to FIG. 1, an abdominal region "AR" of a subject's body generally includes an abdominal wall "AW" having an outer cutaneous or skin layer "s" (e.g., epidermis, dermis, and hypodermis), a fascia layer "f" including connective tissue and an inner muscle layer "m" (e.g., anterior rectus sheath) that enshrouds organs, vessels, and/or other tissue for performing various bodily functions such as digestion. For instance, as part of a digestive system "D" of a subject's body, the stomach "S" and the intestines "I" are supported in the abdominal cavity "AC." In the course of a natural digestion process, the stomach "S" and the intestines "I" collaborate with the rest of the digestive system "D" to process food and excrete fecal matter "P" through the anus "A." Unfortunately, as a result of disease or injury to the intestines "I," for example, it may become necessary to bypass natural digestion through the anus "A" by performing an ostomy through the abdominal region "AB" in order to safely excrete the fecal matter "P" from the intestine "I" of the subject's body.

Figure 2:
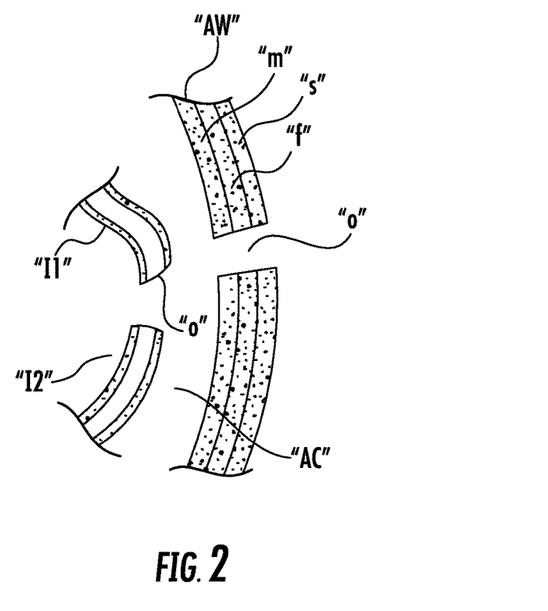
FIG. 2 is a schematic illustration, in partial cross-section, of the abdominal region illustrating an intestine resected and an opening created in the abdominal wall in connection with performing an ostomy procedure in accordance with an illustrative embodiment of the present disclosure.

Referring now to FIG. 2, in accordance with one exemplative methodology of the present disclosure, an internal body organ or vessel, such as the intestine "I", can be accessed through an incision or opening "o" formed, e.g., with a scalpel through the skin layer "s", the fascia layer "f" and the inner muscle layer "m" of the abdominal wall "AW." The clinician introduces one or more instruments through the opening "o" and bisects the intestine "I" into a first intestinal end segment "I1" and a second intestinal end segment "I2". The second intestinal end segment "I2" may be sealed closed with any suitable instrument such as an ultrasonic and/or electrosurgical forceps (not shown). For a detailed description of the construction and operation of one example of such a forceps, reference is made to U.S. Pat. No. 8,444,664, the entire contents of which is incorporated by reference herein.

Figure 3:
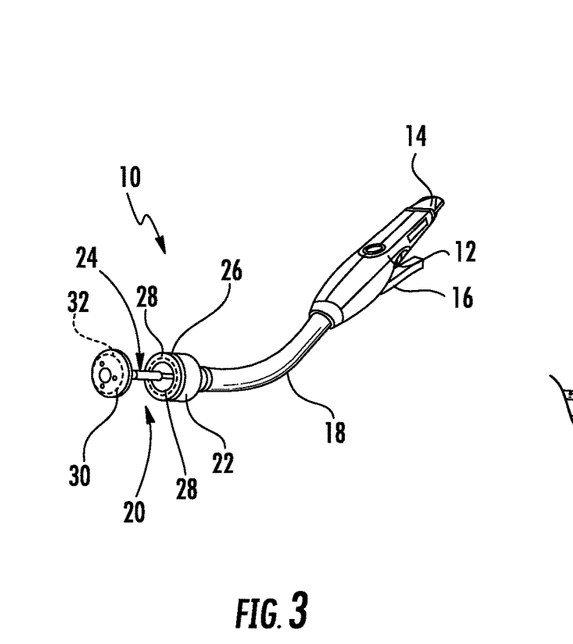
FIG. 3 is a perspective view of an circular anastomosis instrument for use in performing the ostomy procedure.

With the intestine "I" bisected into first and second intestinal end segments "I1", "I2", attention is directed to connecting the first intestinal segment "I1" about the opening "o" within the abdominal wall "AW". In embodiments, the first intestinal end segment "I1" may be secured to the abdominal wall "AW" with a stapling apparatus such as the circular fastener apparatus 10 depicted in FIG. 3. In general, the circular fastener apparatus 10 includes a handle assembly 12 that supports an approximation knob 14 and a firing trigger 16. The circular fastener apparatus 10 further includes an elongated shaft 18 that extends distally from the handle assembly 12 to an end effector assembly 20 supported on a distal end portion of the elongated shaft 18. The end effector assembly 20 includes a shell assembly 22 and an anvil 24 that are movable between an unapproximated position (FIG. 3) and an approximated position in response to rotation of the approximation knob 14 of the handle assembly 12. The shell assembly 22 includes a cartridge 26 that supports an annular array of fasteners (e.g., rectangular and/or round wire staples—not shown) in fastener-retaining slots 28 defined in the cartridge 26. The anvil 24 includes an anvil head 30 defining fastener-forming pockets 32 that are configured to form the fasteners upon firing of the fasteners from the cartridge 26. For a detailed description of the construction and operation of one example of such a circular fastener apparatus, reference is made to U.S. Pat. No. 8,011,554, the entire contents of which is incorporated by reference herein.

Figure 4:
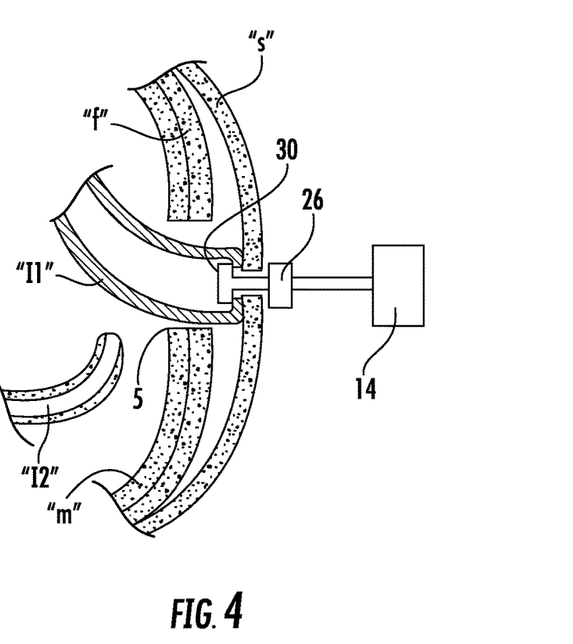
FIG. 4 is a schematic illustration of the intestinal end segment positioned about the anvil head of the circular anastomosis instrument and the fastener cartridge positioned adjacent the opening in the abdominal cavity prior to actuation of the instrument.

With reference to FIG. 4, in one exemplary procedure, the skin layer "s" is separated from the fascia "f" at least along locations adjacent the opening "o". Thereafter, the anvil head 30 of the stapling apparatus 10 is introduced through the opening "o" within the abdominal wall "AW" and positioned within the first intestinal end segment "I1". The first intestinal end segment "I1" is secured about the anvil head 30 with the use of purse string sutures or the like. The cartridge 26 is positioned external of the skin layer "s". The approximation knob 14 is then rotated to move the end effector assembly 20 to the approximated position (FIG. 4) so that an end portion of the first intestinal segment "I1" and the skin layer "s" are clamped between the anvil head 30 and the cartridge 26. The firing trigger 16 of the handle assembly 12 is actuated to fire the fasteners from the fastener-retaining slots 28 of the cartridge 26 for formation against the fastener-forming pockets 32 of the anvil 30 to fasten the first intestinal end segment "I1" to the skin layer "s". The circular fastener apparatus 10 can then be removed.

Figure 5:
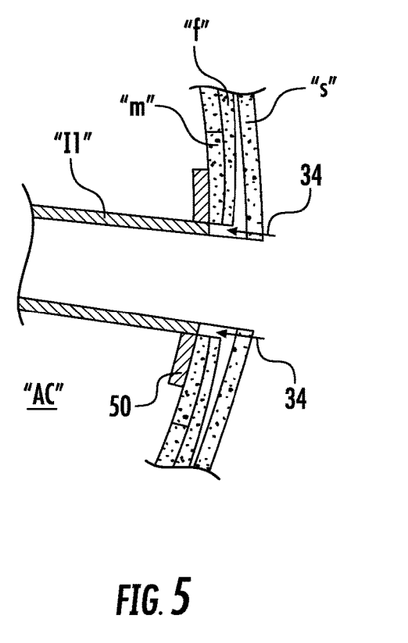
FIG. 5 is a schematic illustration of the intestinal end segment attached to cutaneous tissue subsequent to firing the circular anastomosis instrument to form the ostomy.
Figure 6:
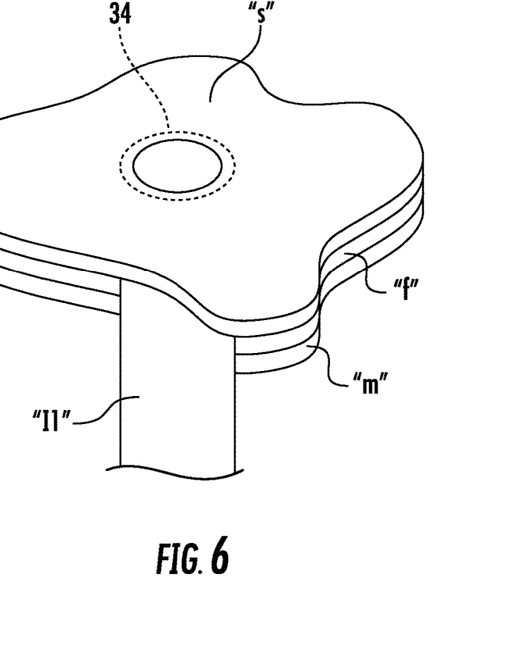
FIG. 6 is a perspective view illustrating the staple line created in the cutaneous tissue for attaching the intestinal end segment and forming the ostomy.

FIGS. 5-6 illustrates the skin layer "s" attached to the first intestinal end segment "I1". The fasteners 34 are depicted schematically and penetrate only the skin layer "s" not the underlying fascia layer "f" or muscle layer "m" to connect to the first intestinal segment "I1" within the abdominal cavity "AC". Thus, the first intestinal segment "I1" does not extend through the opening "o" in the abdominal wall "AW", but, rather is secured to the inner surface of the skin layer "s". Thus, formation of a stoma with the first intestinal segment "I1" on the exterior of the skin layer "s" or outside the abdominal cavity "AC" is avoided along with the accompanying limitations associated therewith, including, e.g., leakage of intestinal fluids, infections and other dermal complications. FIG. 6 illustrates the annular array of fasteners 34 penetrating the skin layer "s" to connect with the first intestinal segment "I1" to form the ostomy. In some embodiments it is contemplated that some fascia tissue of the fascia layer "f" may be captured by the fasteners 34.

In addition, a surgical mesh 50 (e.g., a hernia mesh) (FIG. 5) may be secured to the muscle layer "m" and the first intestinal end segment "I1" to stabilize the first intestinal end segment "I1" within the abdominal cavity "AC" to minimize the potential of herniation. For a detailed description of one example of a hernia mesh, reference is made to U.S. Pat. No. 9,005,308, the entire contents of which is incorporated by reference herein.

Figure 7:
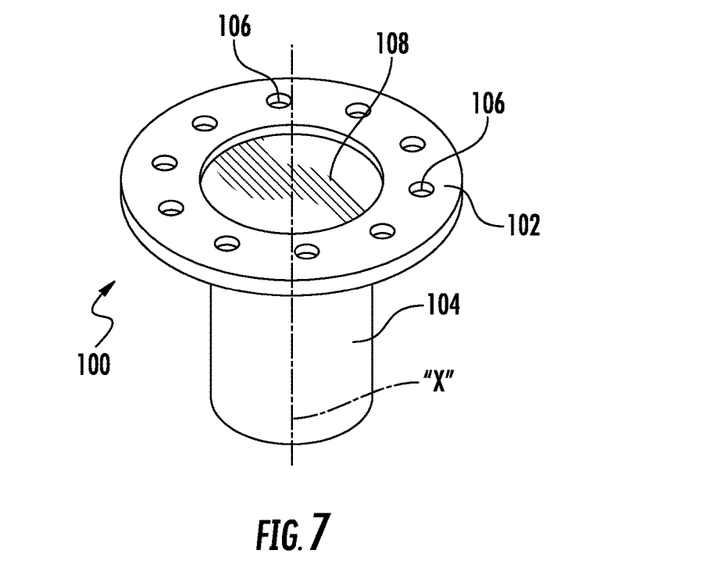
FIG. 7 is a perspective view of an illustrative embodiment of an access device for insertion within the ostomy.

Referring now to FIG. 7, an access device 100 may be mounted to the abdominal wall "AW" in registration with the opening "o" and the first intestinal end segment "I1" to provide a conduit for passage of waste material (e.g., fecal matter "P") to a collection device such as a colostomy or ileostomy bag (not shown). The access device 100 includes a flange segment 102 and a connector segment 104 extending from the flange segment 102 and defining a longitudinal axis "x". The flange segment 102 includes a plurality of spaced openings 106, which, in embodiments may be disposed in equidistant radial spaced relation. The openings 106 are configured to receive fasteners to couple the access device 100 to the skin layer "s". The connector segment 104 may be cylindrical and extends for a distance sufficient to be received through the opening "o" and within the first intestinal end segment "I1". The flange segment 102 and the connector segment 104 define a longitudinal passage 108 therethrough to permit passage of the fecal matter "P" to the collection device.

The access device 100 may be formed from any biocompatible material including stainless steel, titanium or one or more polymers. The biocompatible polymer may be biodegradable, non-biodegradable or a combination of biodegradable and non-biodegradable. The term "biodegradable" as used herein is defined to include both bioabsorbable and bioresorbable materials.

Figure 8:
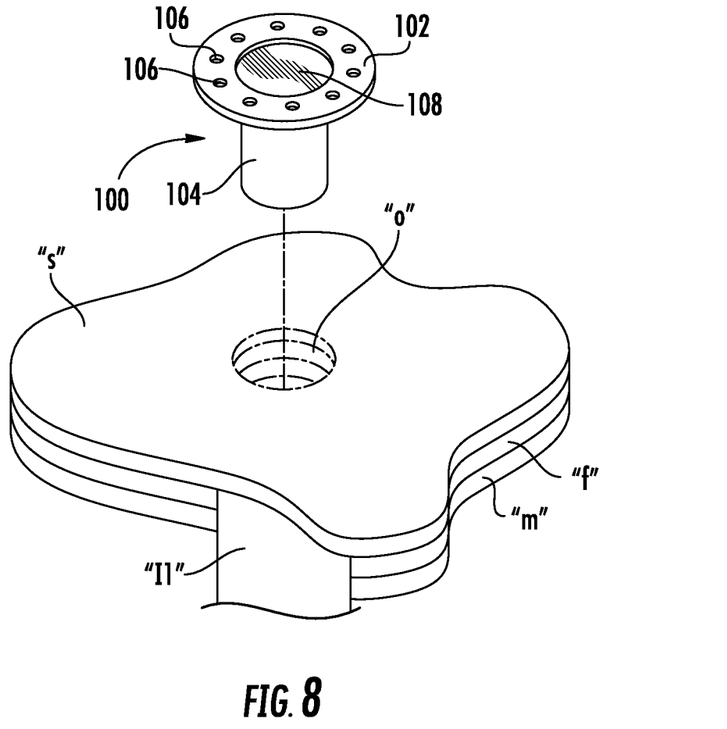
FIGS. 8-9 are perspective views illustrating a sequence of insertion of the access device of FIG. 7 within the ostomy.
Figure 9:
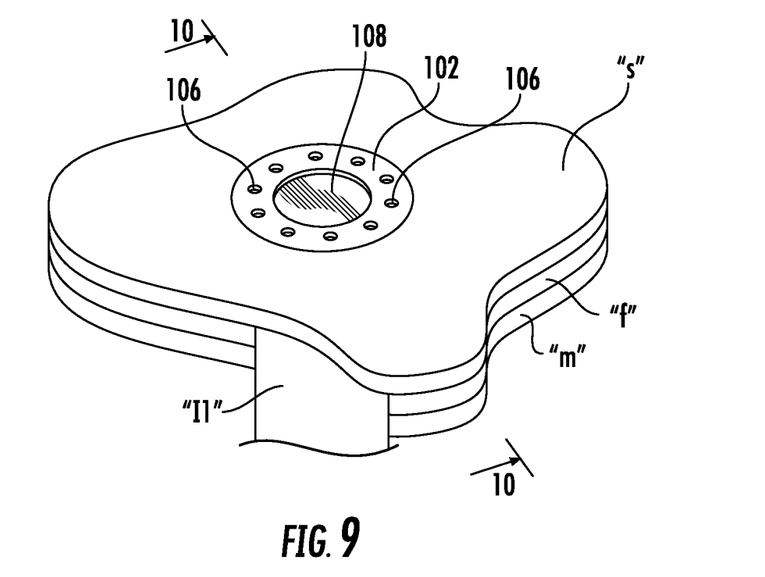
Figure 10:
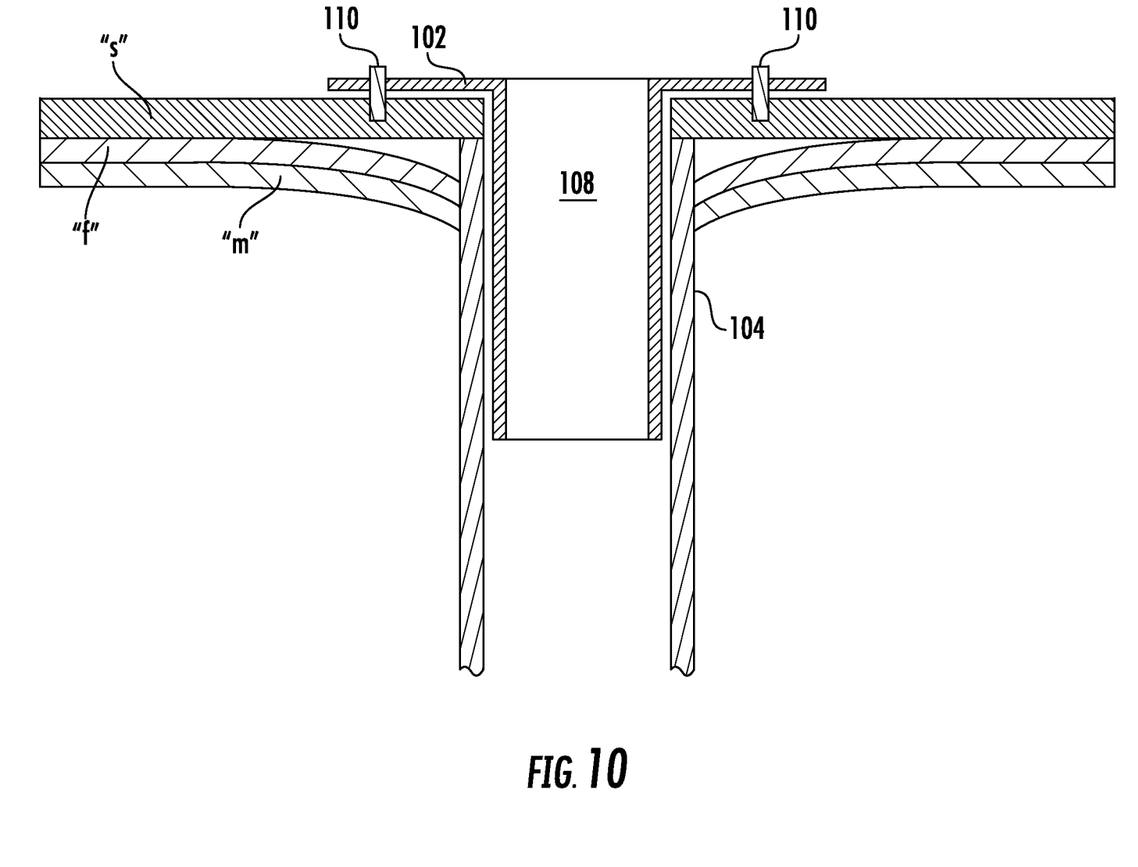
FIG. 10 is a cross-sectional view taken along the lines 10-10 of FIG. 9.
Figure 11:
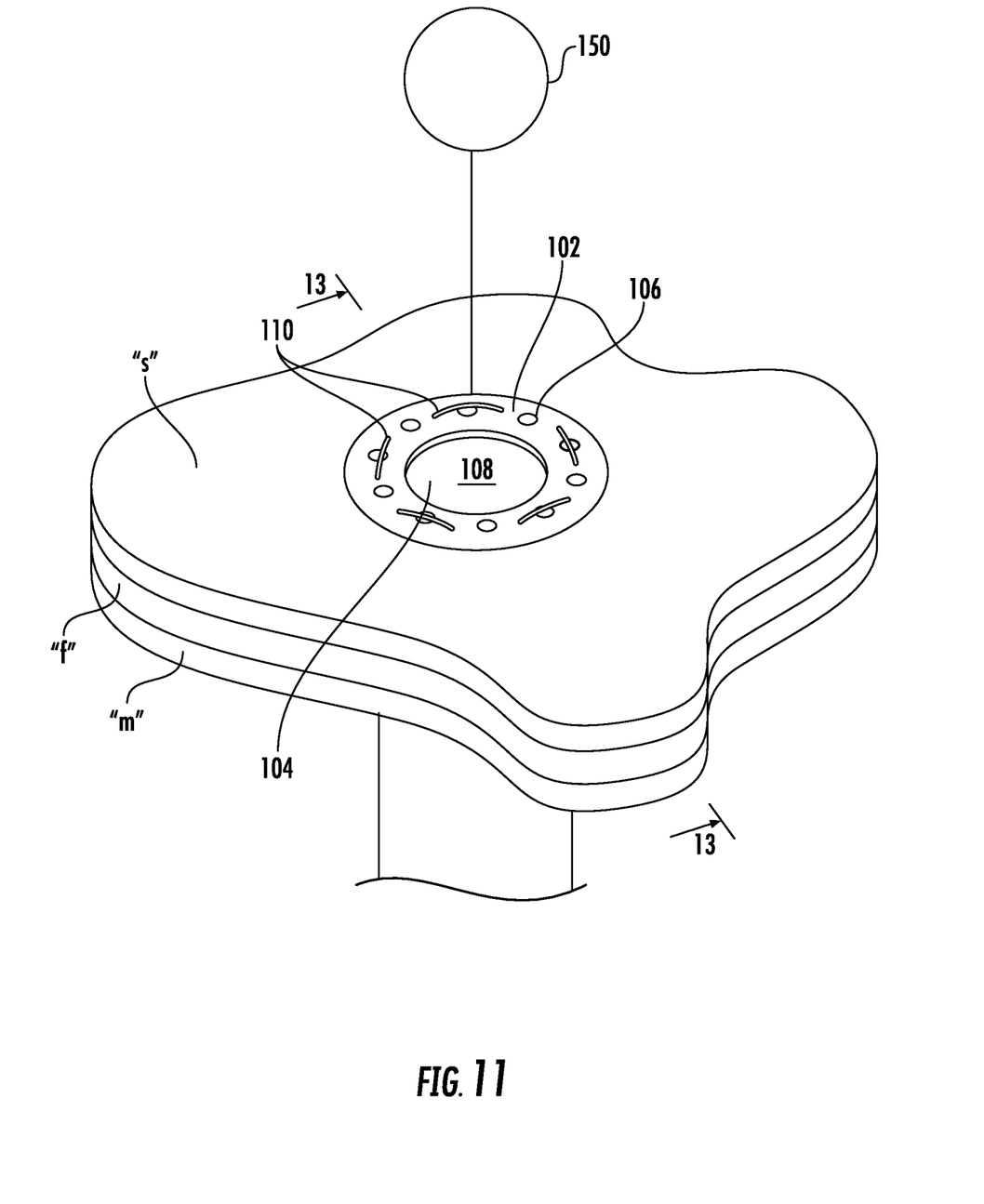
FIG. 11 is a perspective view illustrating securing of the access device to the abdominal wall in registration with the ostomy.

In use, with reference to FIGS. 8-9, the connector segment 104 of the access device 100 is introduced through the opening "o" in the abdominal wall "AW" and the flange segment 102 is positioned against the outer surface of the skin layer "s". In FIGS. 8-9, the fascia layer "f" and inner muscle layer "m" removed for clarity purposes. In embodiments, the connector segment 104 may be secured within the first intestinal segment "I1" with cements, adhesives, etc. which may be applied prior to, or subsequent to, insertion of the connector segment 104 into the first intestinal segment "I1". The connector segment 104 may establish a seal with the internal surface of the first intestinal segment "I1". With the access device 100 appropriately positioned in registration with the first intestinal end segment "I1", the flange segment 102 is secured to the skin layer "s" through application of at least one fastener 110 as depicted in FIGS. 10-11. In embodiments, the circular fastener apparatus 10 described hereinabove in connection with FIG. 3 may be utilized to deliver an annular array of fasteners 110 (e.g., staples) within the flange segment 102. Other instruments for application of the fasteners 110 are disclosed in commonly assigned U.S. Patent Publication Nos.: 2014/0121684 to Criscuolo and 2014/0276972 to Abuzaina et al., the entire contents of each disclosure being incorporated by reference herein. In the alternative, the flange segment 102 may be secured to the skin layer "s" via suturing.

The fasteners 110 may be delivered through the skin layer "s" without penetrating through the underlying fascia layer "f" or muscle layer "m". Thus, the fasteners 110 connect the skin layer "s" directly to the intestinal end segment "I1". It is contemplated, however, that at least some fascia tissue may be captured by the fasteners 110.

With the access device secured relative to the opening "o", a collection device, depicted schematically as reference numeral 150, (FIG. 11) may be mounted to the flange segment 102 of the access device 100. The collection device 150 may be a colostomy bag or the like. Any methodology for mounting the collection device 150 to the flange segment 102 is envisioned. The collection device 150 receives intestinal fluids and/or fecal matter passing through the longitudinal passage 108 of the access device 100.

Thus, the aforedescribed methodology performs an ostomy procedure without requiring inversion and exposure of the intestine as in conventional stoma formation. The access device 100 supports the first intestinal end segment "I1" during treatment and provides a mechanism to attach a collection device 150 without producing undue strain within the opening "o" of the abdominal wall and on the first intestinal segment "I" thereby preserving the integrity of the ostomy. The ostomy is effected by connecting the skin layer "s" directly to the first intestinal end segment "I1" which may be advantages in certain conditions, e.g., in dealing with obese subjects, where access to the muscle layer "m" is limited.

Figure 12:
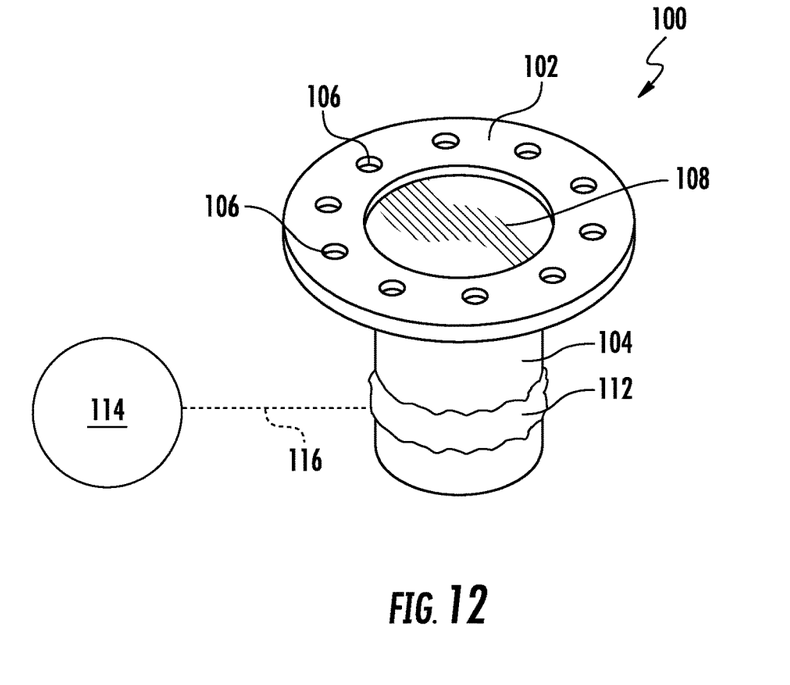
FIG. 12 is a perspective view of one illustrative embodiment of the access device incorporating an external inflatable bladder.
Figure 13:
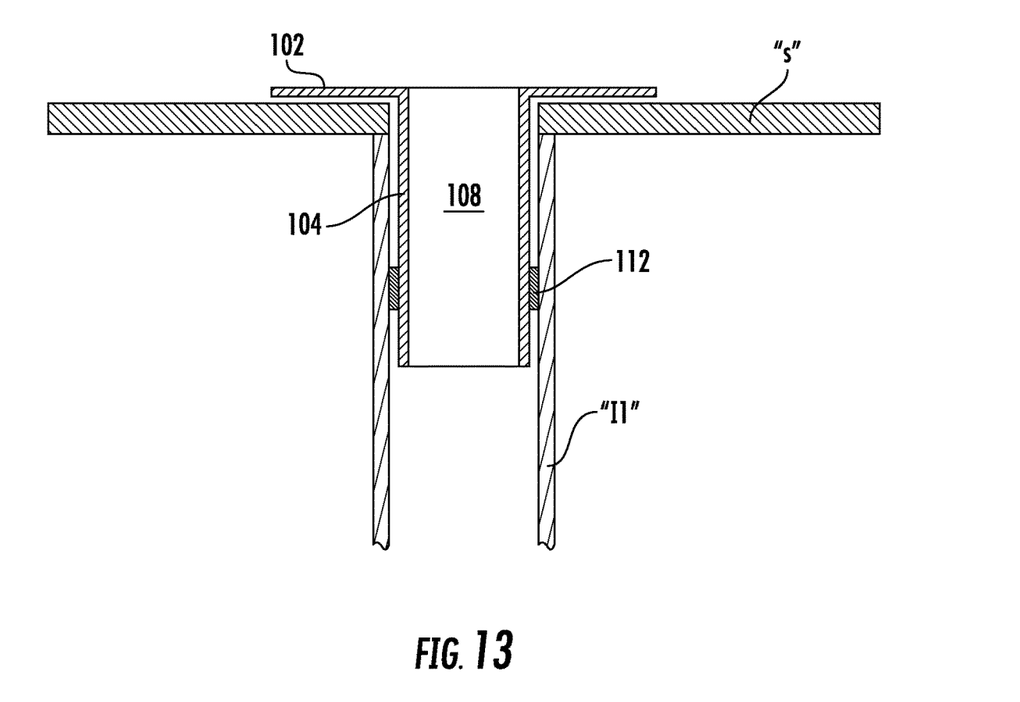
FIG. 13 is a cross-sectional view illustrating the access device of FIG. 12 positioned within an ostomy.

FIGS. 12-13 illustrate an embodiment of an access device for use in the surgical procedure, which may optionally include an inflatable balloon or cuff 112 disposed on the exterior surface of the connector segment 104. The inflatable balloon 112 is in fluid communication with a source of fluids 114 through conduit 116 (shown schematically in FIG. 12). The conduit 116 may be a separate tube extending within the connector segment 102 or, may be a channel extending through the wall of the connector segment 104. The inflatable balloon 112 is configured to transition from the deflated condition depicted in FIG. 11 to the inflated condition depicted in FIG. 12 to engage the internal surface of the first intestinal segment "I1" to secure the connector segment 104 and within the first intestinal end segment "I1". The inflatable balloon 112 also may establish a seal about the connector segment 104 within the first intestinal end segment "I1" to prevent passage of fluids or fecal matter.

Figure 14:
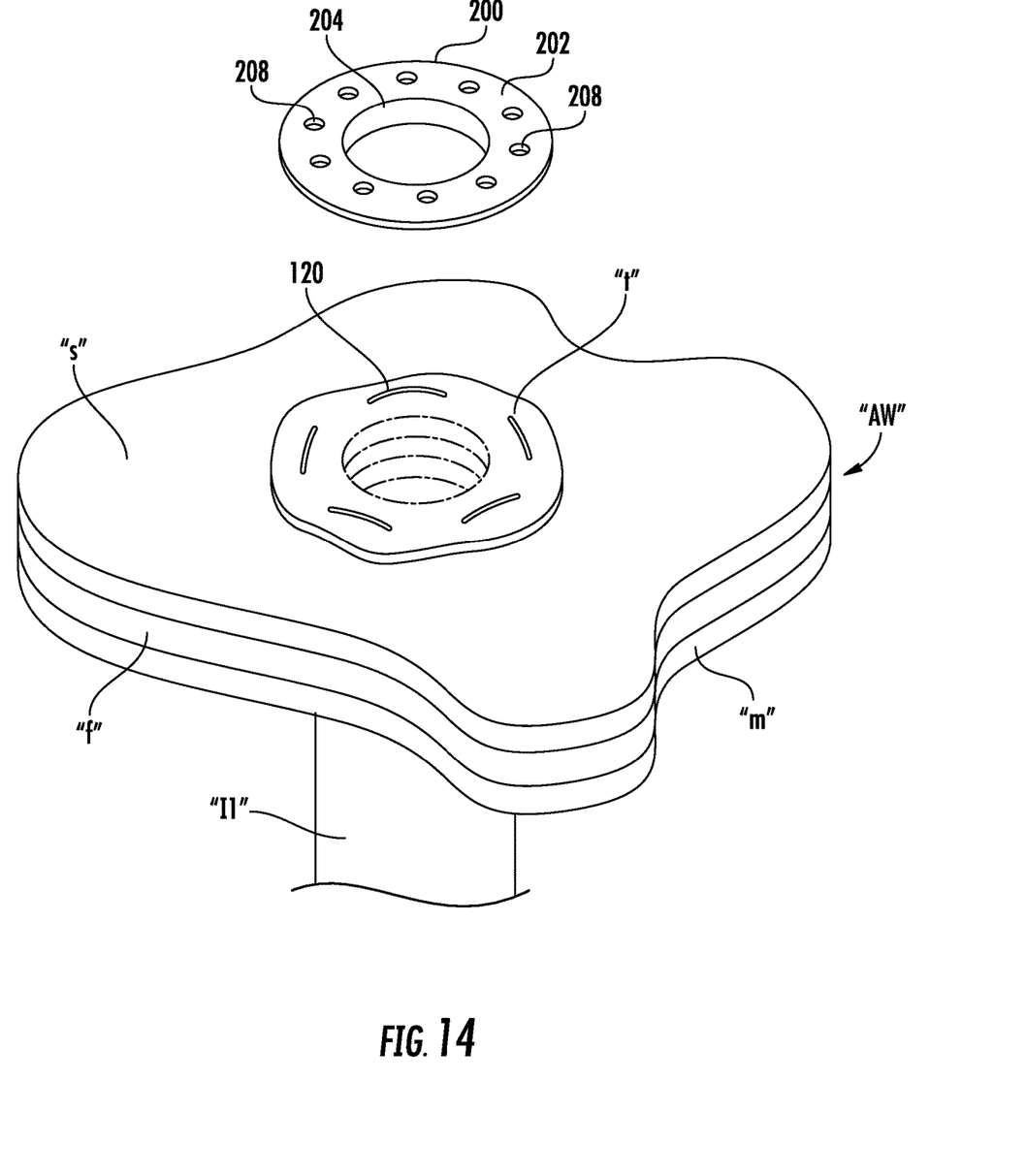
FIG. 14 is a perspective view illustrating an alternative methodology and associated access device for forming an ostomy.
Figure 15:
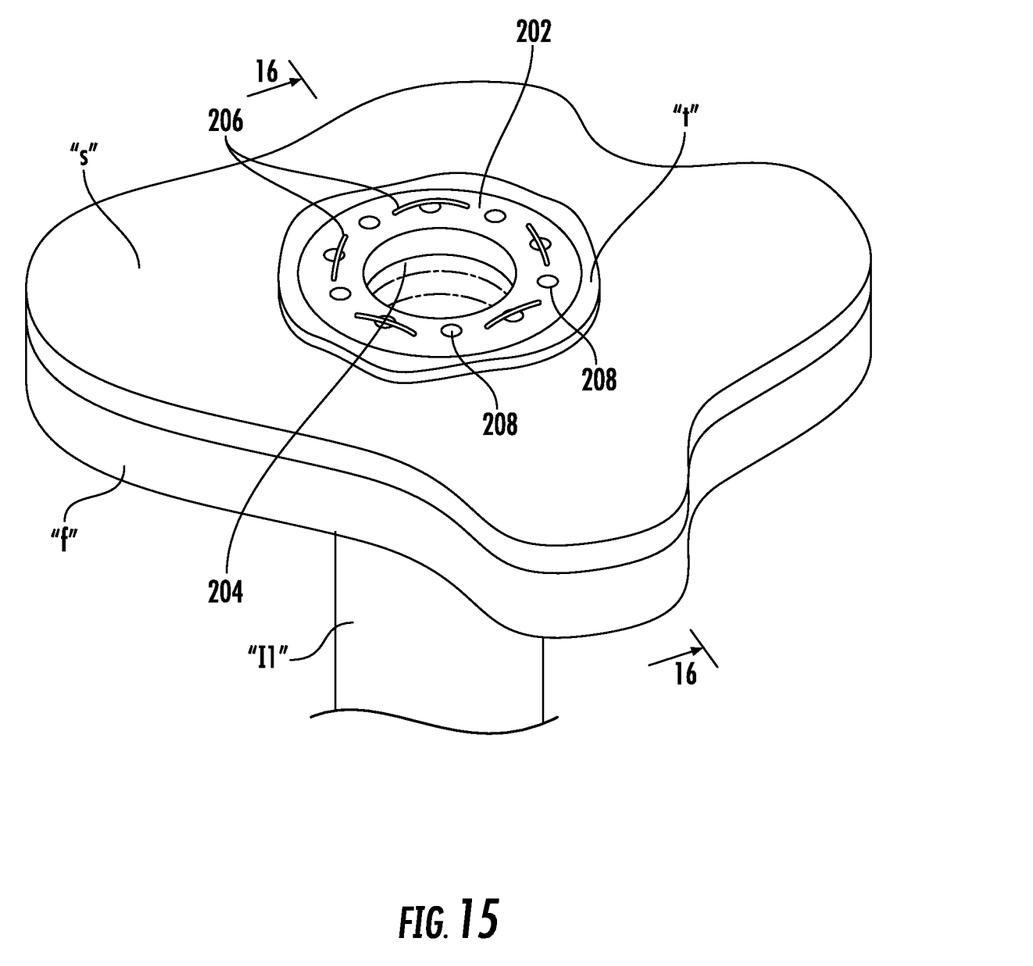
FIG. 15 is a perspective view illustrating insertion of the access device of FIG. 14 within the ostomy.
Figure 16:
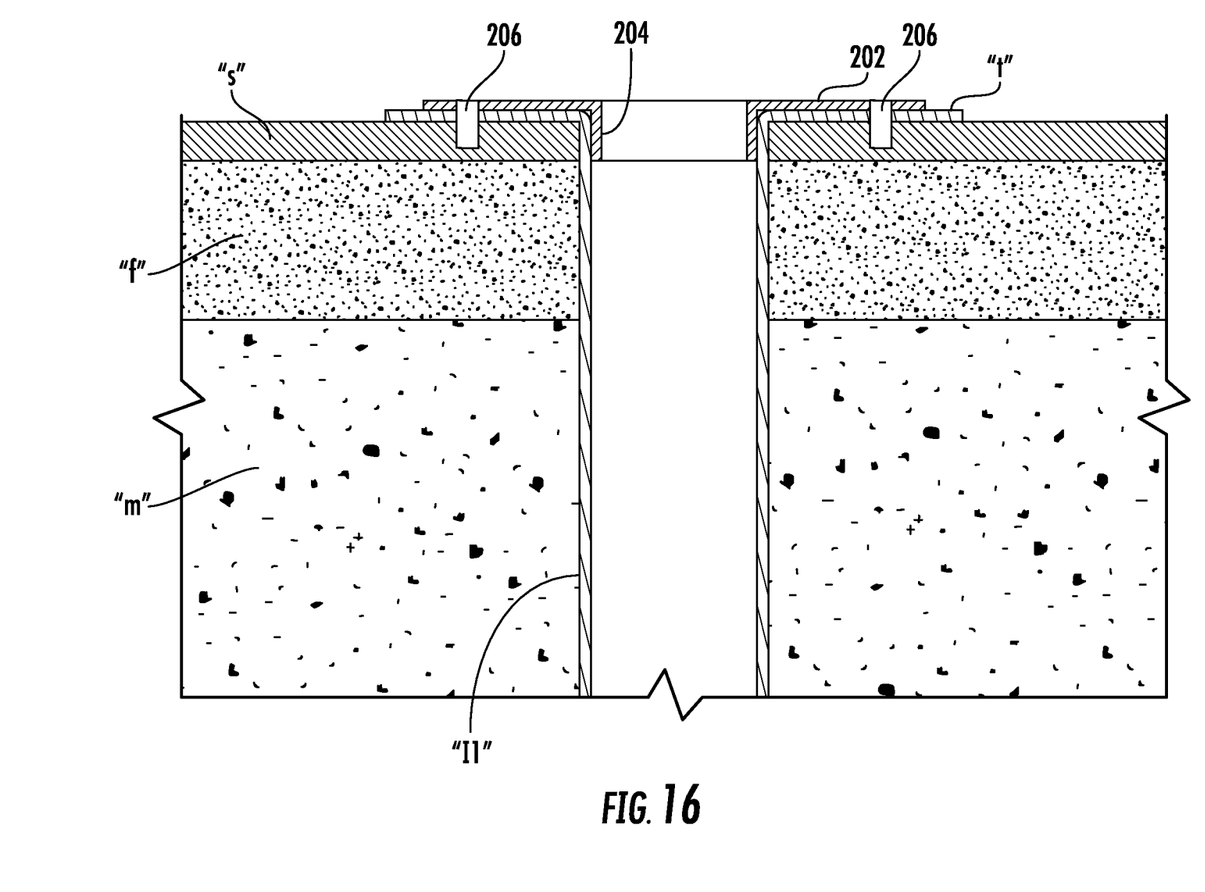
FIG. 16 is a cross-sectional view taken along the line 16-16 of FIG. 15.

FIGS. 14-16 illustrate another methodology and access device for connecting the first intestinal end segment "I1" about the opening "o" within the abdominal wall "AW". In accordance with this methodology, the first intestinal end segment "I1" is pulled through the opening "o" and at least partially inverted as in a conventional stoma formation procedure to establish a stoma "t". An annular array of fasteners 120 may be applied to the tissue of the stoma "t" to connect the first intestinal end segment "I1" and the skin layer "s" in a similar manner discussed hereinafter. In embodiments, the fasteners 120 do not engage or penetrate the underlying fascia layer "f" and muscle layer "m". An access device 200 including a flange segment 202 and a connector segment 204 is positioned relative to the stoma "t". The flange segment 202 is substantially similar to the flange segment 102 of the access device of FIGS. 7-12. The connector segment 204 may be shorter in length than the corresponding connector segment 104 of the access device 100 of FIGS. 7-11. In use, the connector segment 204 is positioned within the opening "o" in the abdominal wall "AW" with the flange segment 202 engaging the outer surface of the skin layer "s". Staples or fasteners 206 are applied through or about the openings 208 in the flange segment 202 to the end margins of the first intestinal end segment "I1" and secure the flange segment 202 to the skin layer "s". The fasteners 206 may also penetrate underlying fascia tissue of the fascia layer "f". A collection device may be coupled to the flange segment 202 as discussed hereinabove.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A method for accessing matter within an intestine, comprising:
    creating an opening extending through a cutaneous layer and a fascia layer of an abdominal wall of an abdominal cavity;
    separating the cutaneous layer from the fascia layer to expose an internal-facing surface of the cutaneous layer;
    accessing an intestinal end segment of an intestine within the abdominal cavity;
    positioning the intestinal end segment of the intestine in registration with the opening extending through the abdominal wall;
    attaching the intestinal end segment directly to the internal-facing surface of the cutaneous layer surrounding the opening to establish fluid communication between a lumen of the intestine and the opening through the abdominal wall;
    securing an access device adjacent the opening through the abdominal wall; and
    connecting a receptacle to the access device configured to be in fluid communication with the lumen of the intestine to collect matter within the intestine.

2. The method of claim 1, further including:
    coupling the intestinal end segment of the intestine to an anvil of a stapling instrument;
    connecting the anvil to the stapling instrument;
    firing the stapling instrument to deliver fasteners through the cutaneous layer surrounding the opening and within the intestinal end segment of the intestine.

3. The method of claim 2, wherein securing the access device includes positioning a connector segment of the access device through the opening and within the lumen of the intestinal end segment of the intestine.

4. The method of claim 3, further including establishing a fluid tight seal about the connector segment of the access device within the lumen of the intestinal end segment of the intestine.

5. The method of claim 4, wherein establishing the fluid tight seal includes inflating an inflatable bladder disposed about the connector segment of the access device to engage an inner wall of the intestinal end segment.

6. The method of claim 4, wherein establishing the fluid tight seal includes suturing the intestinal end segment of the intestine to the connector segment of the access device.

7. The method of claim 4, wherein establishing the fluid tight seal includes adhering the connector segment of the access device within the lumen of the intestinal end segment of the intestine.

8. The method of claim 2, wherein attaching the intestinal end segment of the intestine includes arranging the intestinal end segment about an anvil head of the anvil.

9. The method of claim 8, wherein firing the stapling instrument includes approximating the anvil head relative to a staple cartridge of the stapling instrument.

10. The method of claim 9, wherein firing the stapling instrument includes delivering an annular array of staples, the staples being at least partially deformed by the anvil head of the anvil.

11. The method of claim 10, wherein attaching the intestinal end segment of the intestine includes applying a purse string about the intestinal end segment and the anvil head.

12. The method of claim 2, wherein firing the stapling instrument includes delivering staples through facial tissue underlying the cutaneous layer.

13. The method of claim 2, wherein positioning the intestinal end segment includes exposing end margins of the intestinal end segment external of the opening, and wherein firing the stapling instrument includes delivering the fasteners through the end margins of the intestinal end segment.

14. The method of claim 2, further including attaching a mesh to the intestinal end segment and to muscle tissue beneath the cutaneous layer.

15. The method of claim 1, further comprising inserting the access device into the intestinal end segment.

* * * * *